United States Patent
Lee et al.

[11] Patent Number: 6,103,263
[45] Date of Patent: Aug. 15, 2000

[54] DELAYED PULSE RELEASE HYDROGEL MATRIX TABLET

[75] Inventors: Der-Yang Lee, Plantation; Chih-Ming Chen, Cooper City, both of Fla.

[73] Assignee: Andrx Pharmaceuticals, Inc., Fort Lauderdale, Fla.

[21] Appl. No.: 08/341,478

[22] Filed: Nov. 17, 1994

[51] Int. Cl.[7] ................................... A61K 9/22
[52] U.S. Cl. .................. 424/468; 424/464; 424/465; 424/473; 424/469; 514/777; 514/781
[58] Field of Search ................... 424/473, 468, 424/464

[56] References Cited

U.S. PATENT DOCUMENTS

| | | | |
|---|---|---|---|
| 3,065,143 | 11/1962 | Christenson et al. | 424/468 |
| 4,369,172 | 1/1983 | Schor et al. | 424/468 |
| 4,389,393 | 6/1983 | Schor et al. | 424/469 |
| 4,704,285 | 11/1987 | Alderman | 424/468 |
| 4,871,548 | 10/1989 | Edgren | 424/488 |
| 5,009,895 | 4/1991 | Lui | 424/465 |

OTHER PUBLICATIONS

Metolose SR Brochure ShinEtsu, USP Hydroxypropyl Methylcellulose (1993).
Tech. Info. Sheet for Methoccel, Dow Chemical (1991).

*Primary Examiner*—James M. Spear
*Attorney, Agent, or Firm*—Hedman, Gibson & Costigan, P.C.

[57] ABSTRACT

The invention provides a delayed-pulse controlled release pharmaceutical tablet having:
(a) from 20 to 60 wt. % of a low molecular weight hydroxypropyl cellulose having a number average molecular weight of 70,000 to 90,000;
(b) from 4 to 10 wt. % of a high molecular weight hydroxypropyl cellulose having a number average molecular weight of 1,100,000 to 1,200,000;
(c) a pharmacologically acceptable amount of a medicament; and
(d) an inert solid diluent.

6 Claims, 5 Drawing Sheets

DELAYED PULSE RELEASE HYDROGEL MATRIX TABLET

BACKGROUND OF THE INVENTION

The present invention is concerned with a delayed-pulse release matrix tablet dosage formulation that is characterized by a rapid release of drug during the terminal phase of drug release from a particular tablet. The tablet contains a blend of two different hydroxypropyl cellulose ethers. The combined effect of the selected hydroxypropyl cellulose ethers is to provide a delayed pulse release of an active medicament. The rate of release of the medicament may be controlled by the relative amounts of the different hydroxypropyl cellulose ethers.

In U.S. Pat. No. 4,369,172, which is incorporated by reference, hydroxypropyl methylcellulose having a number average molecular weight ($M_n$) below 50,000, and a hydroxypropyl content of 9–12 wt. % was disclosed as a carrier base for unit dose of a pharmaceutical which provides a regular and prolonged release pattern for a systemically administered absorbable medicament or active ingredient incorporated therein.

U.S. Pat. No. 4,704,285 discloses sustained release pharmaceutical compositions which are based on the use of finely divided hydroxypropyl cellulose which has at least 50 wt. % of the particles passing through a 100 mesh screen.

U.S. Pat. No. 4,369,172 points out that U.S. Pat. No. 3,065,143 discloses the use of hydroxypropyl methylcelluloses having a viscosity of 4000 and 15000 cps as determined by the method described in ASTM D-2363-72 (2 wt. % aqueous solution at 20° C.)

These hydroxypropyl methylcelluloses have a methoxyl content of 28–30 wt. % and 19–24 wt. % respectively and a hydroxylpropyl content of 7.5–12 wt. % and 4–12 wt. % respectively.

U.S. Pat. No. 4,389,393, which is incorporated by reference, describes the use of a hydroxypropyl methylcellulose as a carrier base for pharmaceutical solid unit dose formulations, wherein the carrier base may also include from 0 to 30 wt. % of methyl cellulose, sodium carboxy methylcellulose or another cellulose ether wherein the carrier base is less than one-third by weight of the solid dosage unit form.

The applicants have discovered that if a tablet prepared from a medicament and two types of hydroxypropyl cellulose having different molecular weights, a pharmaceutical formulation is obtained which has excellent delayed-pulse, sustained release characteristics over at least a 12 hour period.

SUMMARY OF THE INVENTION

The invention is directed to a delayed-pulse release pharmaceutical tablet which comprises:
(a) from 20 to 60 wt. % of a low molecular weight hydroxypropyl cellulose having a number average molecular weight of 70,000 to 90,000, and preferably 80,000;
(b) from 4 to 10 wt. % of a high molecular weight hydroxypropyl cellulose having a number average molecular weight of 1,100,000 to 1,200,000; and preferably 1,150,000;
(c) a pharmacologically acceptable amount of a medicament; and
(d) a solid inert diluent.

Therefore, it is a primary object of the invention to provide a novel delayed-pulse release dosage formulation which may be employed with many and varied medicaments to provide for the sustained release of a medicament.

It is also an object of this invention to provide a novel delayed-pulse release tablet in which the release rate is controlled by providing varying amounts of two different types of hydroxypropyl cellulose.

These and other objects of the invention will become apparent from a review of the specification.

DETAILED DESCRIPTION OF THE INVENTION:

The present invention is directed to a delayed-pulse release dosage form which may be made using a blend of two different hydroxypropyl celluloses, one of which has a low molecular weight and the other has a high molecular weight.

The ratio of one type of hydroxypropyl cellulose to the other type of hydroxypropyl cellulose will control the rate of the release of the medicament.

Figure 1:
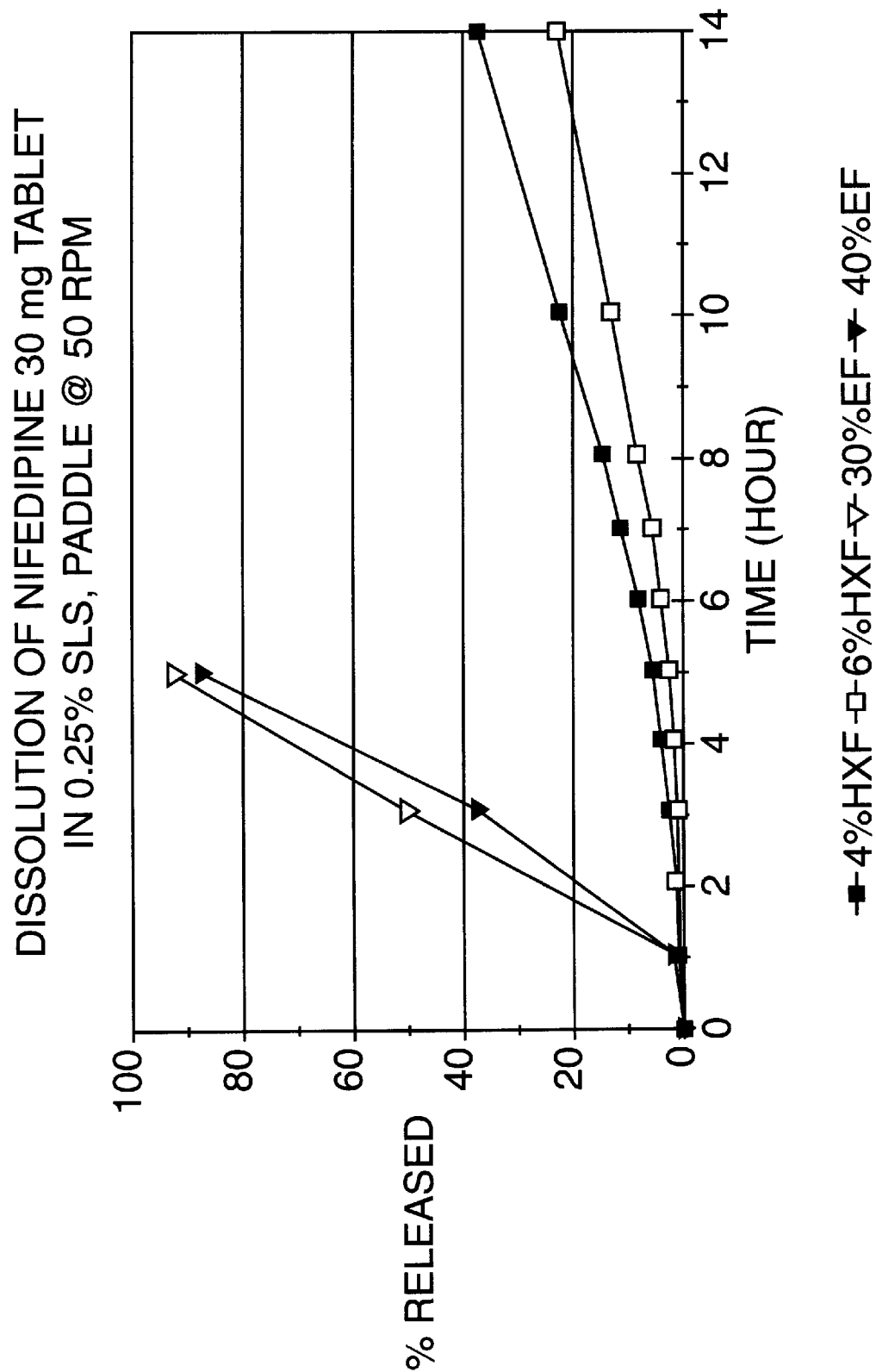
FIG. 1 is a graph of in vitro dissolution data that compares the dissolution rates of 30 mg. tablets of nifedipine which contain either high molecular weight hydroxypropyl cellulose or low molecular weight hydroxypropyl cellulose.

It has been found that the linear dissolution profile is obtained in the presence of either low molecular weight hydroxypropyl cellulose alone or highmolecular weight hydroxypropyl cellulose alone (See FIG. 1) On the other hand, a delayed-pulse release effect is not seen when a hydroxypropyl cellulose of either high or low molecular weight is used alone.

Figure 2:
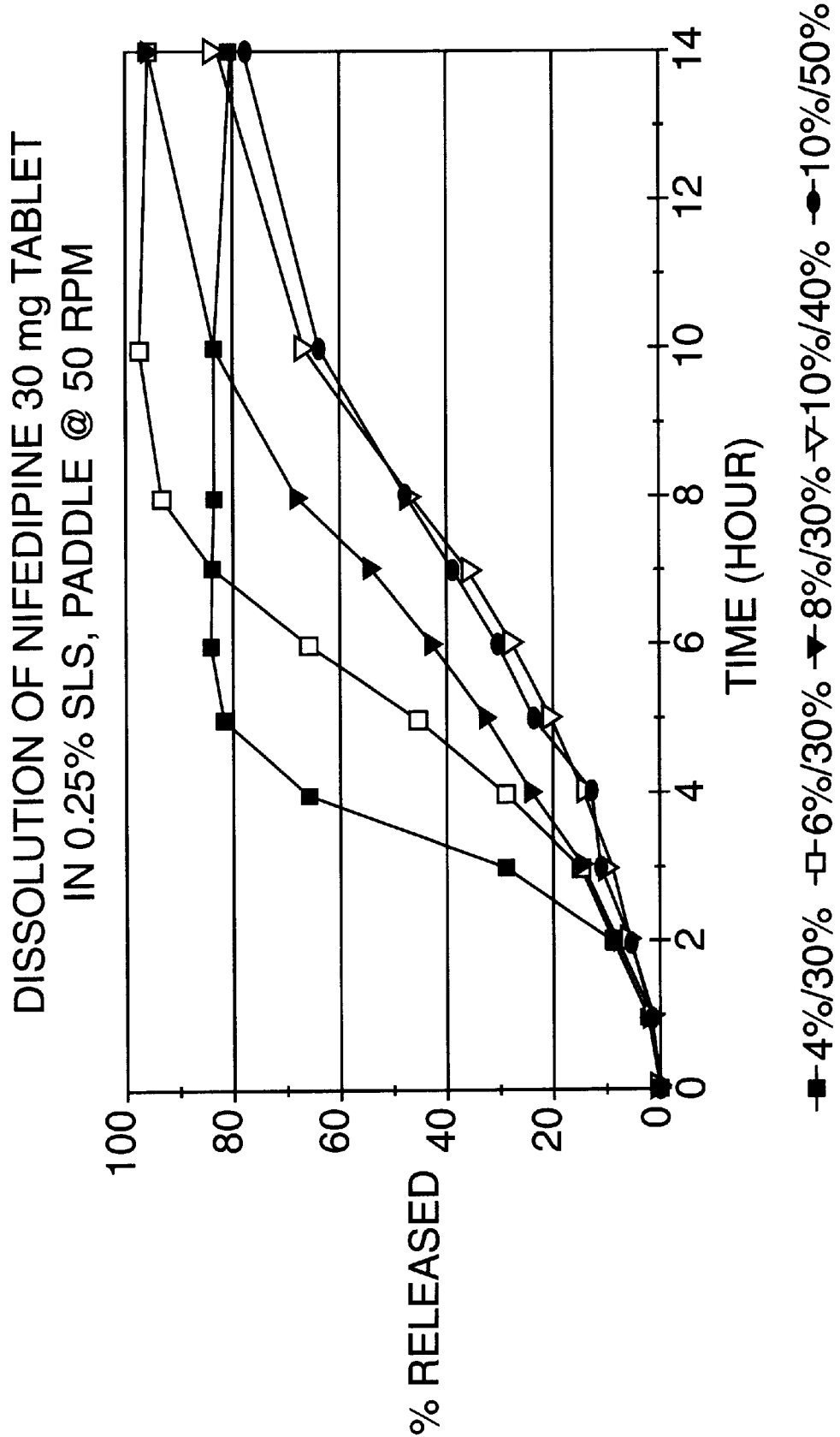
FIG. 2 is a graph of in vitro dissolution data that compares the dissolution rates of 30 mg tablets of nifedipine tablet which contain varying ratios of a low molecular weight/high molecular weight hydroxypropyl celluloses.
Figure 3:
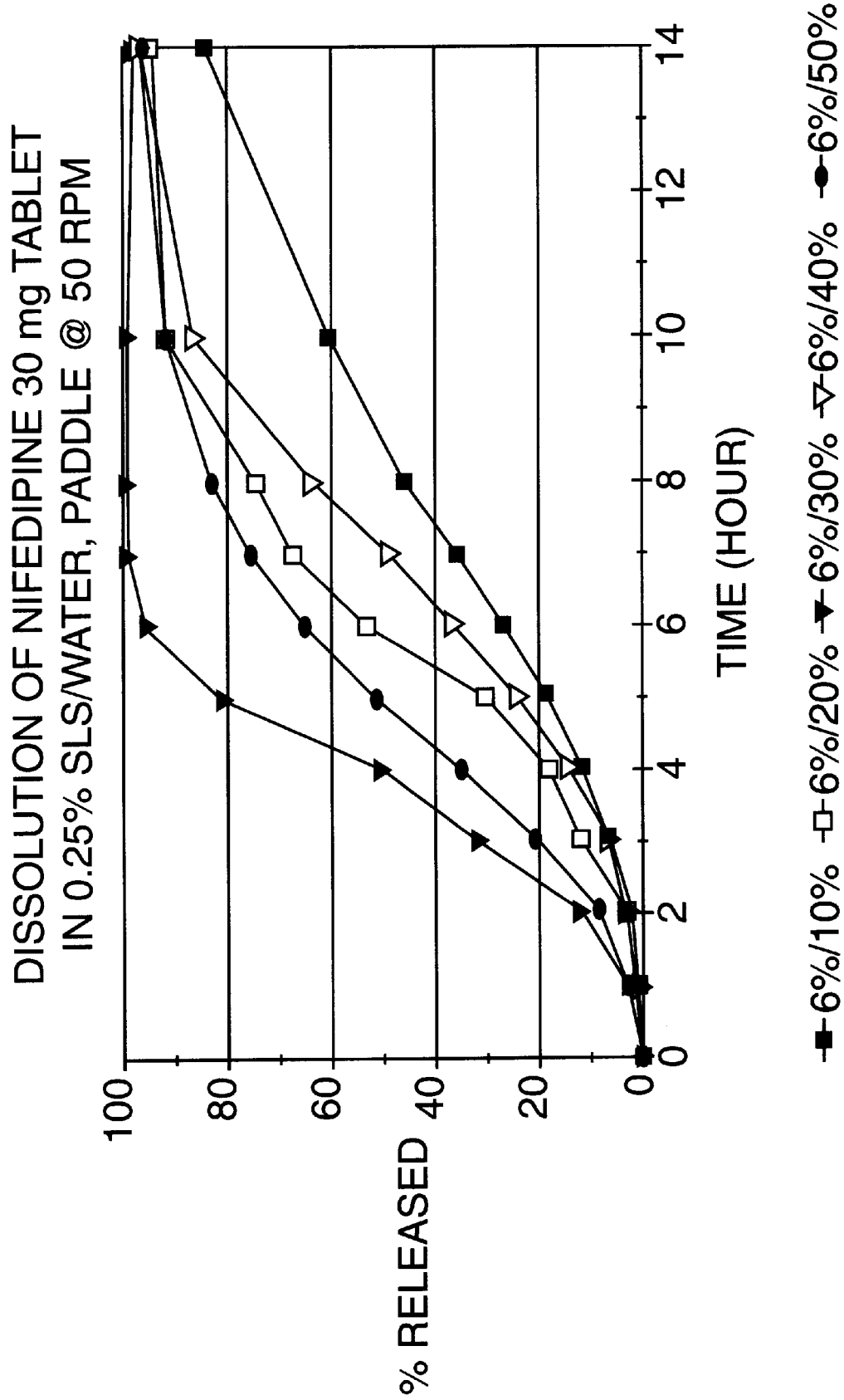
FIG. 3 is a graph of in vitro dissolution data that compares the dissolution rtaes of 30 mg tablets of nifedipine which contain 6 wt % of high molecular weight hydroxypropyl cellulose and varying amounts of low molecular weight hydroxypropyl cellulose.

FIG. 2 shows the effect of the presence of increasing amounts of hyroxypropyl cellulose on the release rate of nifedipine from tablets which contain different amounts of different hydroxypropyl celluloses. The effect is to provide an increase in the rate of the release of the nifedipine from the tablet that is inversely related to the amount of the total weight of all types of hydroxypropyl cellulose in the tablet. The lower the amount of the high molecular weight hydroxypropyl cellulose that is present relative to the amount of the low molecular weight hydroxypropyl cellulose, the faster will be the release rate.

The active medicament that may be formulated according to the method of the present invention may be any inorganic or organic medicament including but not limited to antibiotics, tranquilizers, agents which act on the heart, liver, kidneys, central nervous system, muscles, contraceptives, hormonal agents, antineoplastic agents or combinations of therapeutically complimentary drugs. These drugs are described in the Physicians Desk Reference, 1993 Ed., and U.S. Pat. No. 3,977,404 which are incorporated by reference.

The invention is particularly adaptable to the preparation of sustained release action dosage formulations of water insoluble drugs such as the dihydropyridine calcium channel blockers. These drugs include nifedipine, nilvadipine, nisoldipine, nimodipine, nivadipine, nicardipine and the like. Generally, the ratio of the active medicament to the total weight of hyroxypropyl cellulose in the tablet will be based on a ratio of medicament to hydroxypropyl cellulose that will provide the desired release profile. The ratio of active medicament to the mixture of hydroxypropyl cellulose in the tablet will be about 1:1.6 to 1:8.3 and preferably about 1:4.

The release rates for the tablet of the invention can be selected so that they substantially match the dissolution profile for a commercial nifedipine tablet which has a core and a coated layer without the need to formuale and make a two layer type of tablet.

The pharmacologically acceptable amount of the drug is that amount which is sufficient to deliver a therapeutic plasma level which is sufficient to provide the desired therapeutic result. The dosages for the drugs which are usable according to the present invention are described in the literature and one who is skilled in the art can readily determine the amount of any particular drug which is to be used in the sustained release dosage formulation of the invention by routine experimentation.

The hydroxypropyl cellulose ethers are commercially available or they may be prepared using methods which are described in the chemical literature. The mesh size of the high molecular weight hydroxypropyl cellulose is not critical and generally a high molecular weight hydroxypropyl cellulose in which 85 wt % passes through a mesh size of 100 is preferred. The mesh size of the low molecular weight hydroxypropyl cellulose is also not critical and generally a low molecular weight hydroxylpropyl cellulose in which 95 wt % passes a 30 mesh size is preferred. All references to "mesh" are to U.S. standard mesh.

Other fillers and diluents which are water soluble such as sucrose, mannitol, sorbitol, lactose, dextrose, and the like may also be employed in the tablets of the invention in amounts which provide any required bulk without interfering with the sustained release properties of the tablets of the invention.

A tablet mold lubricant such as magnesium silicate may be added at a level of from 0.25 to 2.5 wt. %. A flow aid may be added to promote an even rate of flow as the the tabletting composition is fed from a hopper to the tablet machine. A finely divided silicon dioxide may be used for this purpose at a level of from 0.25 wt. % to 0.75 wt. %.

The following Examples are merely added to illustrate the invention and are not to be considered as limiting the scope of the invention in any way.

EXAMPLE 1

A series of tablets were prepared which had the following formulations: (all percents are percent by weight of the total weight of the tablet)

| Formulation | A | B | C | D | E |
|---|---|---|---|---|---|
| Nifedipine | 9.8% | 9.8% | 9.8% | 9.8% | 9.8% |
| Lactose % (anhydrous) | 54.7 | 52.7 | 50.7 | 38.7 | 28.7 |
| Hydroxypropyl cellulose[1] | 4% | 6% | 8% | 10% | 10% |
| Hydroxypropyl cellulose[2] | 30% | 30% | 30% | 40% | 50% |
| Magnesium stearate | 1% | 1% | 1% | 1% | 1% |
| Silicon dioxide | 0.5% | 0.5% | 0.5% | 0.5% | 0.5% |

| Formulation | F | G | H | I |
|---|---|---|---|---|
| Nifedipine | 9.8% | 9.8% | 9.8% | 9.8% |
| Lactose % (anhydrous) | 72.7 | 62.7 | 42.7 | 32.7 |
| Hydroxypropyl cellulose[1] | 6% | 6% | 6% | 6% |
| Hydroxypropyl cellulose[2] | 10% | 20% | 40% | 50% |
| Magnesium stearate | 1% | 1% | 1% | 1% |
| Silicon dioxide | 0.5% | 0.5% | 0.5% | 0.5% |

1. Klucel HXF,NF; viscosity 1500–300 cps; 1% soln. 25° C.; $H_2O$ 3@ 30 rpm; $Mw_n$ = 115,000; hydroxy/propyl ratio = 3.4–4.4
Particle size; 60 and above mesh = 0 wt % retained; 80 and above mesh = 6 wt % retained; 100 mesh and above 6.4 wt % retained; total through 100 mesh = 87.6 wt %
2. Klucel EF,NF; viscosity 200–600 cps; (10% soln. $H_2O$, 25° C.) $Mw_n$ = 80,000; hydroxy/propyl ratio = 3.4–4.4
Particle size; 20 and above mesh = 0 wt % retained; 30 and above mesh size = 2.2 wt % retained; total through 30 mesh 97.8 wt %

The magnesium stearate and hydroxypropyl cellulose are separately passed through a #40 mesh sieve. All of the ingredients except the magnesium stearate are separately blended in a V-blender for 10 minutes. The magnesium stearate is then added and the mixture is blended for 3 additional minutes. The tablet is compressed by using a Stokes RD-3 tablet machine with a 0.3410"flat-face beveled edge punch to obtain nifedipine tablets with a hardness of 15+/−5 Kp which each contain 30 mg of nifedipine.

The in vitro dissolution test was conducted in 900 ml of aqueous 0.25 wt. % sodium lauryl sulfate in an apparatus according to the procedure of USPXXII/NFXVII (1990) (which is incorporated by reference) Apparatus 2 with a paddle speed of 50 rpm.

Figure 4:
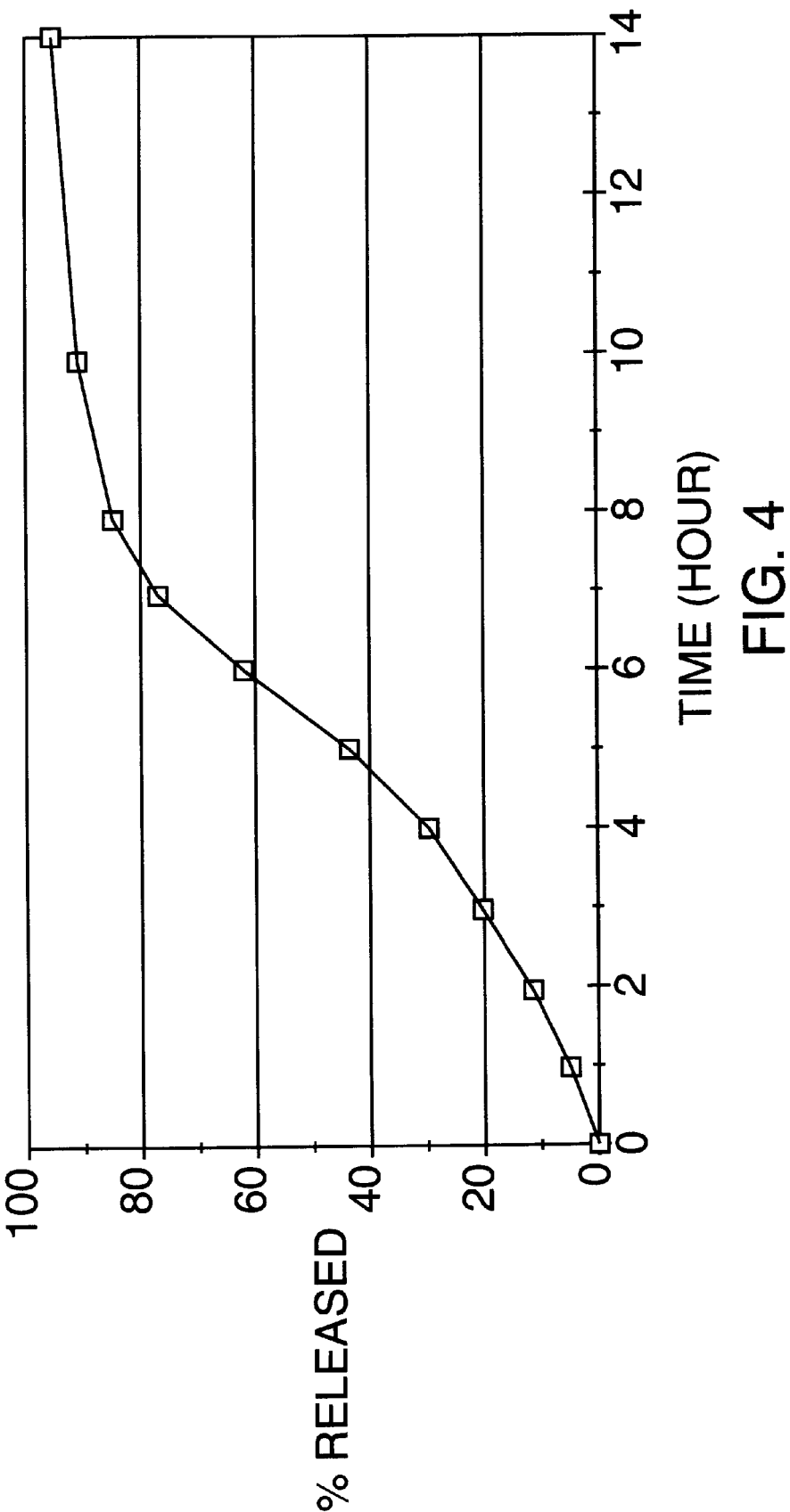
FIG. 4 is a graph of in vitro dissolution data that compares the dissolution profile of 30 mg tablets of nifedipine tablets according to the invention which contain 8 wt. % of high molecular weight hydroxypropyl cellulose and 30 wt. % of low molecular weight hydroxypropyl cellulose.
Figure 5:
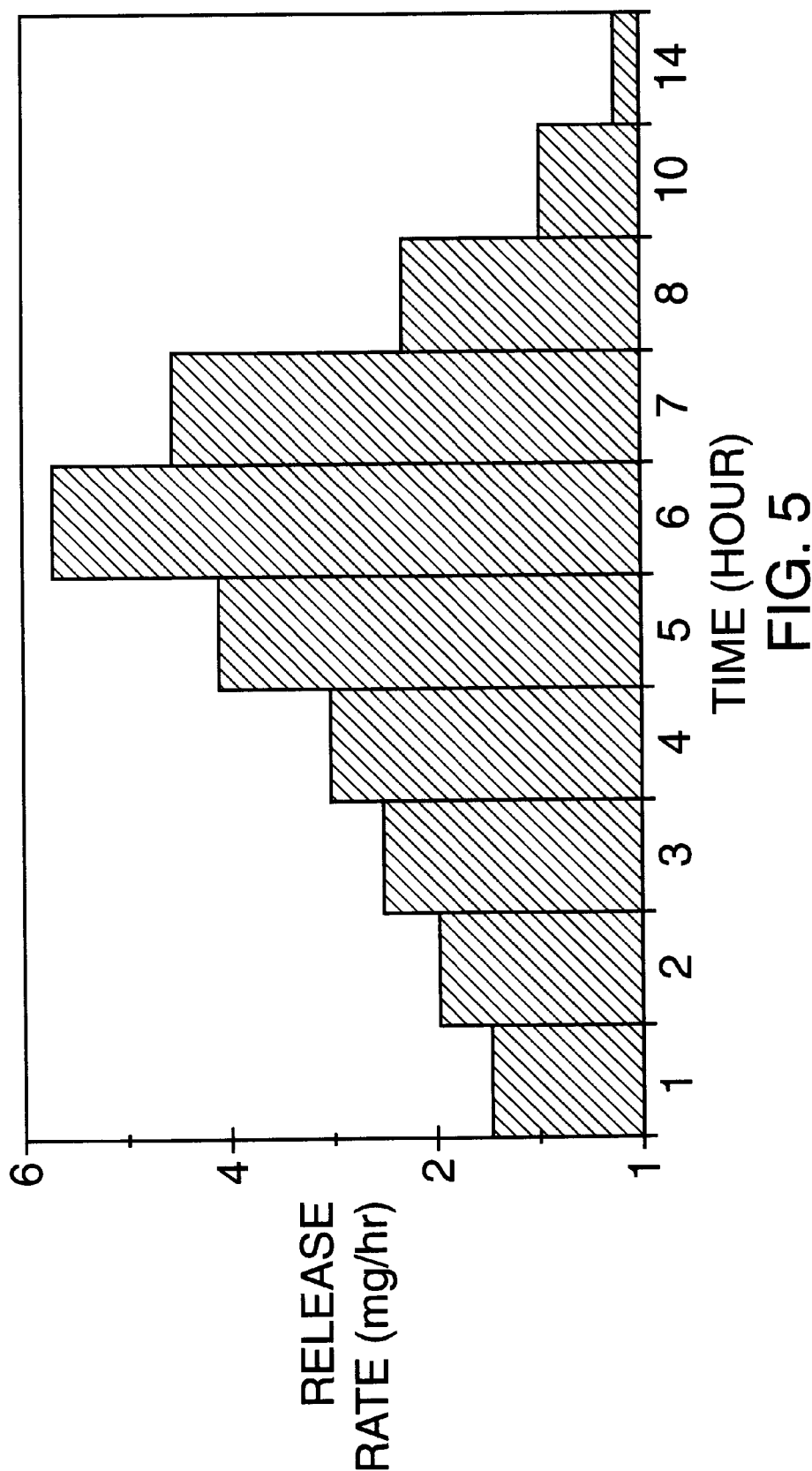
FIG. 5 is a graph of the in vitro release rate for 30 mg tablets of nifedipine according to the invention which contain 8 wt % of high molecular weight hydroxypropyl cellulose and 30 wt % of low molecular weight hydroxypropyl cellulose.

At intervals of from 1 to 14 hours, the weight percent of the nifedipine, which is released when the tablet formulations are dissolved and the aqueous solution in the apparatus described above, is determined and the weight percent of the nifedipine which is released from the tablet is determined and plotted on FIG. 4. The data on FIG. 4 shows inter alia that at 10 hours a formulation according to the present invention (Formulation C) will release about 92 wt. % of the nifedipine.

We claim:

1. A delayed-pulse controlled release pharmaceutical tablet which comprises:

(a) from 20 to 60 wt. % of a low molecular weight hydroxypropyl cellulose having a number average molecular weight of 70,000 to 90,000;

(b) from 4 to 10 wt. % of a high molecular weight hydroxypropyl cellulose having a number average molecular weight of 1,100,000 to 1,200,000;

(c) a pharmacologically acceptable amount of a medicament; and (d) an inert solid diluent.

2. A pharmaceutical delayed-pulse release dosage tablet as defined in claim 1 wherein the medicament is a dihydropyridine.

3. A pharmaceutical delayed-pulse release dosage tablet as defined in claim 2 wherein the inert diluent is selected from the group consisting of sucrose, mannitol, sorbitol, lactose and dextrose.

4. A pharmaceutical delayed-pulse release dosage tablet as defined in claim 2 wherein the tablet has a ratio of from 1:1.6 to 1:8.3 of high molecular weight hydroxypropyl cellulose to low molecular weight hydroxypropyl cellulose.

5. A pharmaceutical delayed-pulse release dosage tablet as defined in claim 3 wherein the inert diluent in the tablet is from 28.7 to 72.7 wt % of the total weight of the tablet.

6. A pharmaceutical delayed-release controlled release dosage tablet as defined in claim 2 wherein the medicament is nifedipine.

* * * * *